(12) United States Patent
Ko et al.

(10) Patent No.: US 9,841,404 B2
(45) Date of Patent: Dec. 12, 2017

(54) PROBE AND MANUFACTURING METHOD THEREOF

(71) Applicant: SAMSUNG MEDISON CO., LTD., Gangwon-do (KR)

(72) Inventors: Jong-Sun Ko, Seoul (KR); Hyun Phill Ko, Seongnam-si (KR); Ki Soo Kim, Seoul (KR); Yong Jae Kim, Gyeongju-si (KR); Jong Mok Lee, Yongin-si (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 99 days.

(21) Appl. No.: 14/749,595

(22) Filed: Jun. 24, 2015

(65) Prior Publication Data

US 2016/0187298 A1 Jun. 30, 2016

(30) Foreign Application Priority Data

Dec. 26, 2014 (KR) .......................... 10-2014-0190374

(51) Int. Cl.
*G10K 11/00* (2006.01)
*G01N 29/24* (2006.01)
*B06B 1/06* (2006.01)
*G10K 11/02* (2006.01)
*G10K 11/30* (2006.01)

(52) U.S. Cl.
CPC ......... *G01N 29/245* (2013.01); *B06B 1/0681* (2013.01); *G10K 11/002* (2013.01); *G10K 11/02* (2013.01); *G10K 11/30* (2013.01)

(58) Field of Classification Search
CPC ........... A61B 8/00; B06B 1/06; B06B 1/0688; G10K 11/004; G10K 11/00; G10K 11/002; G10K 11/20; G10K 9/122; G01N 29/2437

See application file for complete search history.

(56) References Cited

U.S. PATENT DOCUMENTS 5,285,789 A 2/1994 Chen et al.
5,577,507 A 11/1996 Snyder et al.
(Continued)

FOREIGN PATENT DOCUMENTS

DE 4114180 A1 11/1992

OTHER PUBLICATIONS

Extended European Search Report dated Jun. 1, 2016 issued in European Patent Application No. 15176649.0.

*Primary Examiner* — David A Rogers
(74) *Attorney, Agent, or Firm* — McDermott Will & Emery LLP (57) ABSTRACT

Disclosed herein is a probe including: an acoustic module including a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer; a plurality of attenuation layers provided at both edges of the upper surface of the acoustic module, and configured to attenuate ultrasonic waves generated by the acoustic module; and a lens layer disposed to cover the upper surfaces of the attenuation layers, and configured to focus ultrasonic waves transmitted forward from the piezoelectric layer at a predetermined point.

20 Claims, 9 Drawing Sheets

(56) References Cited

U.S. PATENT DOCUMENTS

| | | | |
|---|---|---|---|
| 5,820,564 A | 10/1998 | Slayton et al. | |
| 7,888,847 B2* | 2/2011 | Dietz | G10K 11/30 181/176 |
| 8,773,002 B2* | 7/2014 | Jin | A61B 8/00 310/334 |
| 2005/0046311 A1* | 3/2005 | Baumgartner | B06B 1/0292 310/334 |
| 2005/0272183 A1* | 12/2005 | Lukacs | B06B 1/0622 438/109 |
| 2008/0312537 A1 | 12/2008 | Hyuga | |
| 2012/0056512 A1* | 3/2012 | Jin | A61B 8/00 310/335 |
| 2012/0123274 A1* | 5/2012 | Ikeda | G10K 11/002 600/472 |
| 2013/0200755 A1* | 8/2013 | Kim | H01L 41/047 310/336 |
| 2013/0241356 A1* | 9/2013 | Kim | A61B 8/4444 310/336 |
| 2014/0096610 A1* | 4/2014 | Ha | G10K 11/00 73/632 |

* cited by examiner

PROBE AND MANUFACTURING METHOD THEREOF

CROSS-REFERENCE TO RELATED APPLICATION

This application claims priority from Korean Patent Application No. 10-2014-0190374, filed on Dec. 26, 2014 in the Korean Intellectual Property Office, the disclosure of which is incorporated herein in its entirety by reference.

BACKGROUND

1. Field

Apparatuses and methods consistent with exemplary embodiments relate to a probe of transmitting and receiving ultrasonic waves, and a manufacturing method thereof.

2. Description of the Related Art

An ultrasonic imaging apparatus transmit ultrasonic waves to a target region of an object from the surface of the object, and receives echo ultrasonic waves reflected from the target region so as to non-invasively acquire slice images about soft tissue of the object or images about blood vessels of the object based on the echo ultrasonic waves.

The ultrasonic imaging apparatus has advantages that it is a compact, low-priced apparatus and it can display images in real time, compared to other medical imaging apparatuses, such as an X-ray apparatus, a Computerized Tomography (CT) scanner, a Magnetic Resonance Image (MRI) apparatus, and a nuclear medical diagnostic apparatus. Also, the ultrasonic imaging apparatus has high safety since there is no risk for patients to be exposed to radiation such as X-rays. For the advantages, the ultrasonic imaging apparatus is widely used to diagnose the heart, abdomen, urinary organs, uterus, etc.

The ultrasonic imaging apparatus includes a probe to transmit ultrasonic waves to an object and to receive echo ultrasonic waves reflected from the object, in order to acquire ultrasound images of the object.

SUMMARY

One or more exemplary embodiments provide a probe which can form a narrow bandwidth in a short-range region by providing a layer including at least one of a low attenuation material and a high attenuation material, and a method of manufacturing the probe.

It is another aspect of the present disclosure to provide a probe which can realize apodization physically in order to improve the image quality of ultrasound images, and a method of manufacturing the probe.

Additional aspects of the disclosure will be set forth in part in the description which follows and, in part, will be obvious from the description, or may be learned by practice of the exemplary embodiments.

In accordance with one aspect of an exemplary embodiment, a probe includes: an acoustic module including a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer; a plurality of attenuation layers provided at both edges of the upper surface of the acoustic module, and configured to attenuate ultrasonic waves generated by the acoustic module; and a lens layer disposed to cover the upper surfaces of the attenuation layers, and configured to focus ultrasonic waves transmitted forward from the piezoelectric layer at a predetermined point.

The attenuation layers may include a high attenuation material.

Each attenuation layer may have a multi-layer structure, and include a low attenuation material.

The attenuation layers may be arranged on a part of the left upper surface of the acoustic module and on a part of the right upper surface of the acoustic module, respectively, as seen in an elevation direction of the probe.

The attenuation layers may be arranged on the most left upper part of the left upper surface of the acoustic module and on the most right upper part of the right upper surface of the acoustic module, respectively.

The attenuation layers may include a silicon material.

The piezoelectric layer may be formed on a caved surface of the backing layer.

The lens layer may be configured with a plurality of layers.

The piezoelectric layer may be formed on the entire or a part of the upper surface of the backing layer.

In accordance with another aspect of the present disclosure, a probe includes: an acoustic module including a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer; an attenuation layer disposed on the center upper surface of the acoustic module, and including a low attenuation material; and a lens layer disposed to cover the upper surface of the attenuation layer, and configured to focus ultrasonic waves transmitted forward from the piezoelectric layer at a predetermined point.

The attenuation layer may be disposed on the center surface of the acoustic module, as seen in an elevation direction of the probe.

The attenuation layer may include a silicon material.

The piezoelectric layer may be formed on a caved surface of the backing layer.

The attenuation layer may be configured with a plurality of layers, and the lens layer may be configured with a plurality of layers.

The piezoelectric layer may be formed on the entire or a part of the upper surface of the backing layer.

In accordance with another aspect of the present disclosure, a probe includes: an acoustic module including a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer; an attenuation layer disposed on the upper surface of the acoustic module, wherein a center part of the attenuation layer has ultrasonic waves attenuation that is different from ultrasonic waves attenuation of both edges of the attenuation layer; and a lens layer disposed to cover the upper surface of the attenuation layer, and configured to focus ultrasonic waves transmitted forward from the piezoelectric layer at a predetermined point.

The attenuation layer may include a low attenuation material at the center part as seen in an elevation direction of the probe, and a high attenuation material at both edges as seen in the elevation direction of the probe.

The attenuation layer may include a low attenuation material, the center part of the attenuation layer as seen in an elevation direction of the probe may have a single-layer structure, and both edges of the attenuation layer as seen in the elevation direction of the probe may each have a multi-layer structure.

The attenuation layer may include a silicon material.

The piezoelectric layer may be formed on a caved surface of the backing layer.

The attenuation layer may be configured with a plurality of layers, and the lens layer may be configured with a plurality of layers.

In accordance with another aspect of the present disclosure, a method of manufacturing a probe includes: fabricating an acoustic module by forming a backing layer, a piezoelectric layer, and a matching layer sequentially; forming a plurality of attenuation layers configured to attenuate ultrasonic waves generated by the acoustic module, respectively, at both edges of the upper surface of the acoustic module; and forming a lens layer configured to focus ultrasonic waves transmitted forward from the piezoelectric layer at a predetermined point, on the upper surfaces of the attenuation layers.

The forming of the attenuation layers may include forming the attenuation layers with a high attenuation material.

The forming of the attenuation layers may include forming a multi-layer structure each layer formed with a low attenuation material.

The forming of the attenuation layers may include forming the attenuation layers respectively at a part of the left upper surface of the acoustic module and at a part of the right upper surface of the acoustic module, as seen in an elevation direction of the probe.

The forming of the attenuation layers may include forming the attenuation layers respectively at the most left upper part of the left upper surface of the acoustic module and at the most right upper part of the right upper surface of the acoustic module.

The attenuation layers may include a silicon material.

The fabricating of the acoustic module may include removing a part of the backing layer, and forming the piezoelectric layer on a caved surface of the backing layer formed by removing the part of the backing layer.

The forming of the lens layer may include configuring the lens layer with a plurality of layers.

BRIEF DESCRIPTION OF THE DRAWINGS

The above and/or other aspects will become more apparent by describing certain exemplary embodiments with reference to the accompanying drawings, in which.

DETAILED DESCRIPTION

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail FIG. 1 is a perspective view of an ultrasonic imaging apparatus according to an exemplary embodiment, and FIG. 2 is a block diagram of an ultrasonic imaging apparatus according to an exemplary embodiment.

Figure 1:
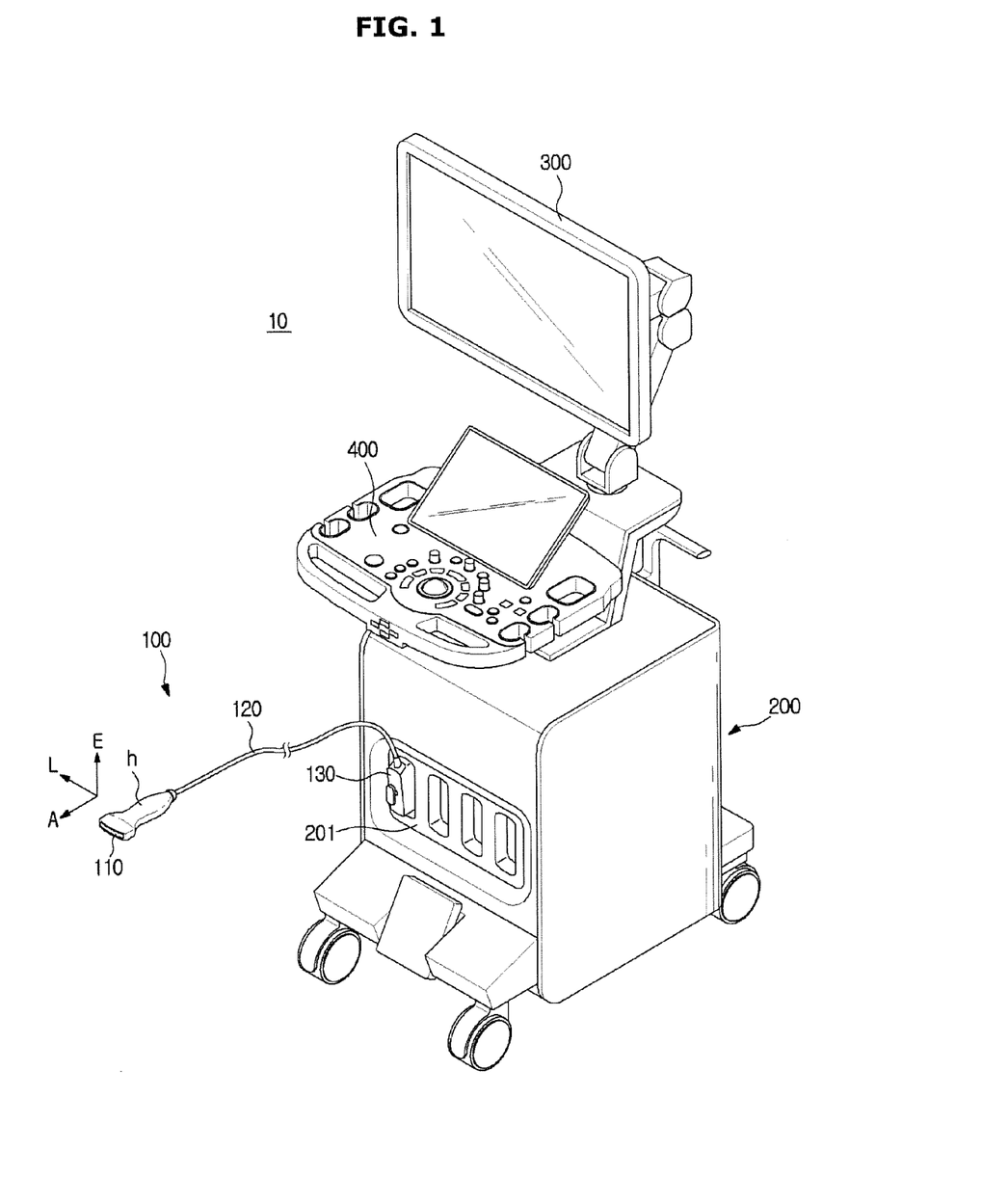
FIG. 1 is a perspective view of an ultrasonic imaging apparatus according to an exemplary embodiment.
Figure 2:
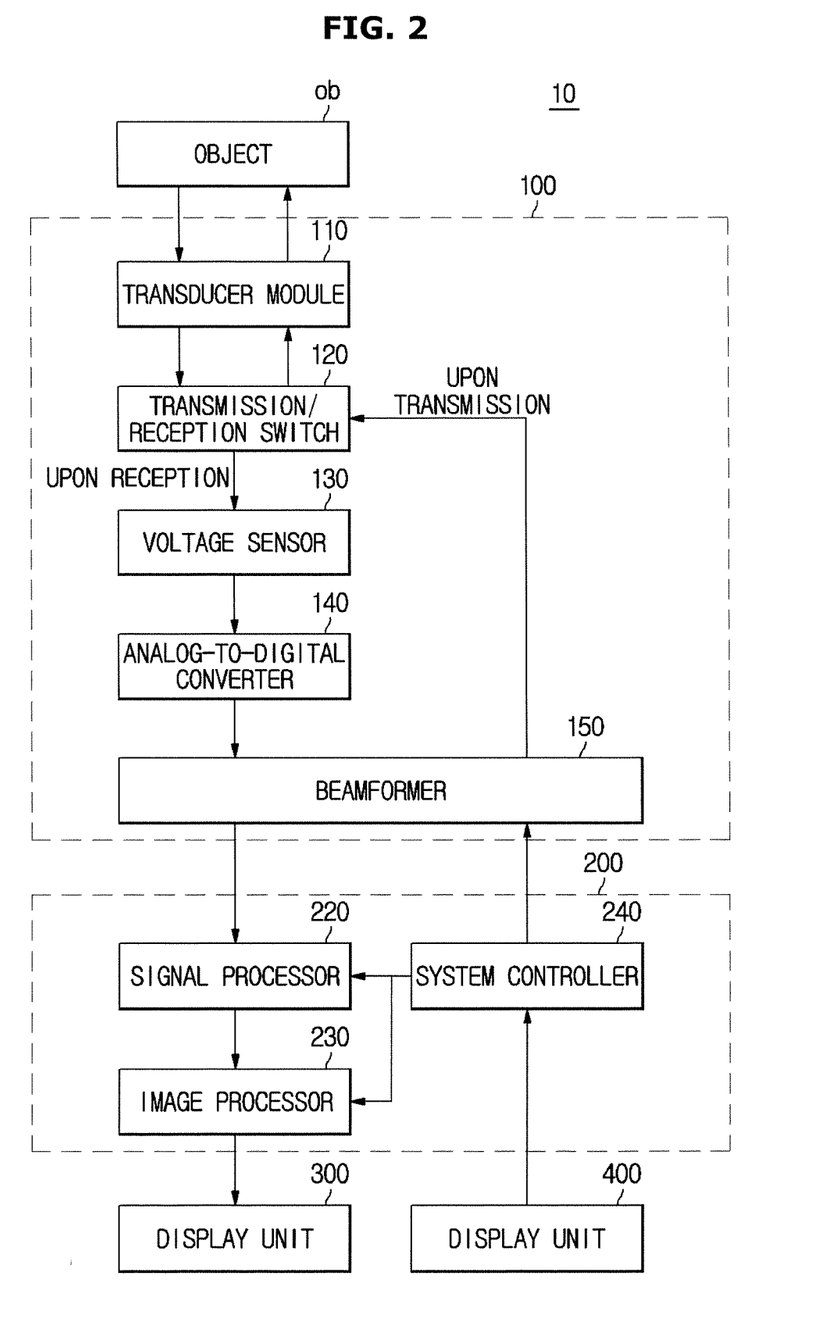
FIG. 2 is a block diagram of an ultrasonic imaging apparatus according to an exemplary embodiment.

Referring to FIG. 1, an ultrasonic imaging apparatus 10 may include a probe 100 and a main body 200. The main body 200 may be connected to the probe 100, and may be a workstation including a display unit 300 and an input unit 400.

Hereinafter, the probe 100 will be described.

The probe 100 may include: a transducer module 110 installed in a housing h, and configured to transmit ultrasonic waves to an object ob, to receive echo ultrasonic waves reflected from the object ob, and to convert electrical signals into ultrasonic waves and vice versa; a male connector 102 physically coupled with a female connector provided in the main body 200, and configured to transmit and receive signals to and from the main body 200; and a cable 101 configured to connect the male connector 102 to the transducer module 110.

Herein, the object ob may be a human's or animal's body part, or tissue in a body part, such as vessels, bonds, and muscles. However, the object ob is not limited to these, and may be anything whose inner structure can be imaged by the ultrasonic imaging apparatus 10.

Diagnosis modes may include an Amplitude mode (A-mode), a Brightness mode (B-mode), a Doppler mode (D-mode), an Elastography mode (E-mode), a Motion mode (M-mode), and a Cadence Pulse Sequencing mode (CPS-mode), although not limited to these.

The echo ultrasonic waves may be ultrasonic waves reflected from the object ob to which ultrasonic waves have been transmitted, and may have various frequency bands or energy levels to produce various ultrasound images according to diagnosis modes.

The transducer module 110 may generate ultrasonic waves according to applied alternating current power. More specifically, the transducer module 110 may receive alternating current power from an external power supply or from an internal power storage unit, for example, a battery. Vibrators of the transducer module 110 may vibrate according to the alternating current power to generate ultrasonic waves.

Three directions forming right angles with respect to the center of the transducer module 110 can be defined as an axial direction A, a lateral direction L, and an elevation direction E, respectively. More specifically, a direction in which ultrasonic waves are transmitted is defined as an axial direction A, a direction in which the transducer module 110 is aligned in a row is defined as a lateral direction L, and the remaining direction perpendicular to the axial direction A and the lateral direction L is defined as an elevation direction E.

The transducer module 110 may be a magnetostrictive ultrasonic transducer using the magnetostrictive effect of a magnetic material, a piezoelectric ultrasonic transducer (PUT) using the piezoelectric effect of a piezoelectric material, a Capacitive Micromachined Ultrasonic Transducer (cMUT) that transmits and receives ultrasonic waves using vibration of several hundreds or thousands of micromachined thin films, or a Piezoelectric Micromachined Ultrasonic Transducer (pMUT).

One end of the cable 101 may be connected to the transducer module 110, and the other end of the cable 101 may be connected to the male connector 102, so as to connect the transducer module 110 to the male connector 102.

The male connector 102 may be connected to the other end of the cable 101 to be physically coupled with a female connector 201 of the main body 200.

The male connector 102 may transfer electrical signals generated by the transducer module 110 to the female connector 201, or may receive control signals generated by the main body 200 from the female connector 201.

However, if the probe 100 is a wireless probe, the cable 101 and the male connector 102 may be not needed, and the probe 100 may transmit and receive signals to and from the main body 200 through a wireless communication module (not shown) included in the probe 100. That is, the probe 100 is not limited to the structure shown in FIG. 1.

Meanwhile, referring to FIG. 2, the probe 100 may further include a beamformer 150, a transmission/reception switch 120, a voltage sensor 130, and an analog-to-digital converter 140, which are installed in the housing h.

The transmission/reception switch 120 may convert an operation mode to a transmission mode upon transmission of ultrasonic waves, or to a reception mode upon reception of ultrasonic waves, according to a control signal from a system controller 240 of the main body 200.

The voltage sensor 130 may sense current output from the transducer module 110. The voltage sensor 130 may be an amplifier to amplify a voltage according to output current.

The voltage sensor 130 may further include a pre-amplifier (not shown) to amplify an analog signal with a small magnitude, wherein the pre-amplifier may be a Low Noise Amplifier (LNA).

The voltage sensor 130 may further include a Variable Gain Amplifier (not shown) to control a gain value according to an input signal, wherein the VGA may be Time Gain Compensation (TGC) to compensate for a gain according to a focal point or a distance to a focal point, although not limited to the TGC.

The analog-to-digital converter 140 may convert an analog voltage output from the voltage sensor 130 into a digital signal.

As shown in FIG. 2, a digital signal converted by the analog-to-digital converter 140 may be input to the beamformer 150, however, an analog signal delayed by the beamformer 150 may be input to the analog-to-digital converter 140.

Also, as shown in FIG. 2, the analog-to-digital converter 140 may be included in the probe 100, however, the analog-to-digital converter 140 may be included in the main body 200. In this case, the analog-to-digital converter 140 may convert an analog signal focused by an adder into a digital signal.

Also, the beamformer 150 may apply appropriate delay times to transmitted ultrasonic waves or received echo ultrasonic waves, in order to enable ultrasonic waves generated by the transducer module 110 to be focused at a target point of an object ob at a desired time, or to compensate for differences between times at which echo ultrasonic waves reflected from the target point of the object ob arrive at the transducer module 110.

The beamformer 150 may be included in the probe 100 corresponding to a front-end, as shown in FIG. 2. However, the beamformer 150 may be included in the main body 200 corresponding to a back-end. Also, the entire or a part of components of the beamformer 150 may be included in any one of the front-end and the back-end.

The main body 200 may accommodate components required to control the probe 100 or to produce ultrasound images based on signals received from the probe 100. The main body 200 may be connected to the probe 100 through the cable 101 (see FIG. 1).

Hereinafter, a signal processor 220, an image processor 230, and a system controller 240 included in the main body 200, the display unit 330, and the input unit 400 will be described in detail.

The signal processor 220 may convert focused digital signals received from the probe 100 into a format suitable for image processing. For example, the signal processor 220 may perform filtering for removing noise signals except for a desired frequency band.

Also, the signal processor 220 may be implemented as a Digital Signal Processor (DSP), and may perform envelope detection for detecting the magnitudes of echo ultrasonic waves based on focused digital signals to generate ultrasound image data.

The image processor 230 may produce an ultrasound image based on the ultrasound image data generated by the signal processor 220 so that a user, for example, a doctor or a patient can visually examine the inside of an object ob, for example, a human body.

The image processor 230 may transfer the ultrasound image created using the ultrasound image data to the display unit 300.

According to another embodiment, the image processor 230 may further perform additional image processing on the ultrasound image. For example, the image processor 230 may further perform post-processing on the ultrasound image, such as correcting or adjusting the contrast, brightness, or sharpness of the ultrasound image.

The additional image processing may be performed according to predetermined settings or according to a user's instruction or command input through the input unit 400.

The system controller 240 may control overall operations of the ultrasonic imaging apparatus 10. For example, the system controller 240 may control operations of the signal processor 220, the image processor 230, the probe 100, and the display unit 300.

According to embodiments, the system controller 240 may control operations of the ultrasonic imaging apparatus 10 according to predetermined settings, or may generate a predetermined control command according to a user's instruction or command input through the input unit 400 to control operations of the ultrasonic imaging apparatus 10.

The system controller 240 may include a processor, Read Only Memory (ROM) to store control programs for controlling the ultrasonic imaging apparatus 10, and Random Access Memory (RAM) to store ultrasound image data or signals input to the probe 100 of the ultrasonic imaging apparatus 10 or the input unit 400, and used as a storage area for various tasks that are performed by the ultrasonic imaging apparatus 10.

In addition, there may be provided a graphic processing board (not shown) including the processor, the RAM, or the ROM on a separate circuit substrate electrically connected to the system controller 240.

The processor, the RAM, and the ROM may be connected to each other through internal buses.

Also, the system controller 240 can be used as a term indicating any component including the processor, the ROM, and the RAM.

Also, the system controller 240 can be used as a term indicating any component including the processor, the ROM, the RAM, and the graphic processing board.

The main body 200 may include at least one female connector 201 (see FIG. 1), and the female connector 201 may be connected to the probe 100 through the cable 101 and the male connector 102.

The display unit 300 may display ultrasound images produced by the image processor 230 so that a user can visually examine the inside structure or tissue of an object ob.

The input unit 400 may receive a predetermined instruction or command for controlling the ultrasonic imaging apparatus 10, from a user. The input unit 400 may include a user interface, such as a keyboard, a mouse, a trackball, a touch screen, or a paddle.

Hereinafter, details about the configuration of the transducer module 110 according to an embodiment of the present disclosure will be described with reference to FIGS. 3 to 5.

Figure 3:
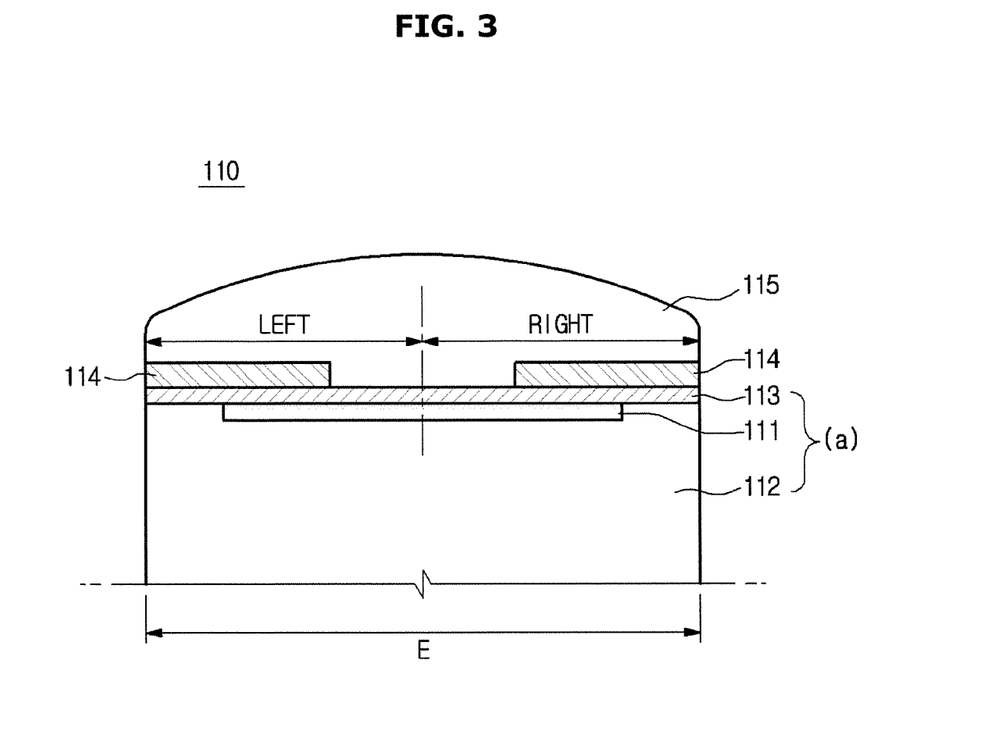
FIG. 3 is a cross-sectional view of a transducer module according to an exemplary embodiment, cut in an elevation direction.

FIG. 3 is a cross-sectional view of a transducer module according to an embodiment of the present disclosure, cut in an elevation direction E.

Referring to FIG. 3, a transducer module 110 according to an embodiment may include: an acoustic module a including a piezoelectric layer 111, a backing layer 112 disposed below the piezoelectric layer 111, and a matching layer 113 disposed on the piezoelectric layer 111; a plurality of attenuation layers 114 arranged to cover both edges of the upper surface of the acoustic module a; and a lens layer 115 disposed to cover the upper surfaces of the attenuation layers 114.

The piezoelectric layer 111 may be formed with a piezoelectric material to convert electrical signals into mechanical vibrations to generate ultrasonic waves.

A phenomenon in which a voltage is generated when a mechanical pressure is applied to a specific material is called a piezoelectric effect, and a phenomenon in which mechanical deformation occurs when a voltage is applied to a specific material is called a converse piezoelectric effect. Materials having the piezoelectric effect and converse piezoelectric effect are piezoelectric materials.

That is, piezoelectric materials are materials capable of converting electricity energy into mechanical vibration energy and vice versa.

The piezoelectric material may be a ceramic of lead zirconate titanate (PZT), a PZMT single crystal containing a solid solution of lead magnesium niobate and lead titanate, or a PZNT single crystal containing a solid solution of lead zincniobate and lead titanate.

The piezoelectric layer 111 may emit mechanical vibration energy as ultrasonic waves in a direction (hereinafter, forward) in which the lens layer 115 is located and in a direction (hereinafter, backward) in which the backing layer 112 is located.

The piezoelectric layer 111 may have a single-layer structure or a multi-layer structure.

The backing layer 112 may be disposed below the piezoelectric layer 111. The backing layer 112 may absorb ultrasonic waves generated by the piezoelectric layer 111 and transmitted backward to block ultrasonic waves from being transmitted backward from the piezoelectric layer 111, thereby preventing image distortion.

The backing layer 112 may have smaller acoustic impedance than the piezoelectric layer 111. For example, the backing layer 112 may be formed with a material having acoustic impedance ranging from 2MRayl to 5MRayl.

The backing layer 112 may be configured with a plurality of layers in order to improve the effect of attenuating or blocking ultrasonic waves.

The matching layer 113 may be disposed on the piezoelectric layer 111. The matching layer 113 may reduce a difference in acoustic impedance between the piezoelectric layer 111 and an object ob to match the acoustic impedance of the piezoelectric layer 111 with the acoustic impedance of the object ob so that ultrasonic waves generated by the piezoelectric layer 111 can be effectively transferred to the object ob.

For this, the matching layer 113 may be formed with a material having smaller acoustic impedance than that of the piezoelectric layer 111 and greater acoustic impedance than that of the object ob.

For example, the matching layer 113 may be formed with glass or a resin material.

Also, the matching layer 113 may be configured with a plurality of layers so that acoustic impedance can change gradually from the piezoelectric layer 111 toward the object ob, and in this case, the plurality of layers configuring the matching layer 113 may be formed with different materials.

Meanwhile, the piezoelectric layer 111 and the matching layer 113 may be machined in a matrix form of a 2Dimensional (2D) array by a dicing process, or may be machined in the form of a 1Dimensional (1D) array.

The plurality of attenuation layers 114 may be arranged to cover both edges of the upper surface of the acoustic module a.

According to an embodiment, the attenuation layers 114 may be formed with a high attenuation material or a high viscosity material in order to attenuate ultrasonic waves generated by the piezoelectric layer 111. For example, the attenuation layers 114 may be formed with a silicon material having attenuation ranging from 20 dB/cm to 40 dB/cm with respect to ultrasonic waves having a frequency of 5 MHz or a driving signal of the transducer module 110. As such, by forming the attenuation layers 114 with a high attenuation material, it is possible to improve the sensitivity of ultrasonic waves.

Also, according to another embodiment, the attenuation layers 114 may have a multi-layer structure each layer formed with a low attenuation material or a low viscosity material in order to attenuate ultrasonic waves like a high attenuation material, which is not shown in the drawings. The low attenuation material or the low viscosity material forming any one layer of the multi-layer structure of the attenuation layers 114 may be a silicon material having attenuation ranging from 3 dB/cm to 15 dB/cm with respect to ultrasonic waves having a frequency of 5 MHz or a driving signal of the transducer module 110.

Herein, the high attenuation material means a material having high ultrasonic waves attenuation compared to the lens layer 115 which will be described later, and the low attenuation material means a material having low ultrasonic waves attenuation compared to the lens layer 115.

The attenuation layers 114 may be, when the upper surface of the acoustic module a is divided into a left upper surface LEFT and a right upper surface RIGHT as seen in the elevation direction E, arranged to cover a part of the left upper surface LEFT and a part of the right upper surface RIGHT, respectively. For example, the attenuation layers 114 may be arranged to cover the most left upper part of the left upper surface LEFT and the most right upper part of the right upper surface RIGHT.

The lens layer 115 may be disposed to cover the upper surfaces of the attenuation layers 114 and the upper surface of the acoustic module a. The lens layer 115 may focus ultrasonic waves transmitted forward from the transducer module 110 at a predetermined point.

The lens layer 115 may be formed with a material that has high wear resistance and can propagate ultrasonic waves at high speed in order to focus ultrasonic waves and protect the acoustic module a, specifically, the piezoelectric layer 111. The lens layer 115 may have a convex shape in the transmission direction of ultrasonic waves in order to focus ultrasonic waves. However, the lens layer 115 may have a concave shape if the velocity of the ultrasonic waves in the air is lower than that in an object ob.

In the current embodiment, a case in which the probe 100 includes a single lens layer 115 and two attenuation layers 114 arranged at both edges of the acoustic module a is shown, however, the probe 100 may include a plurality of lens layers 115 having different properties.

Figure 4:
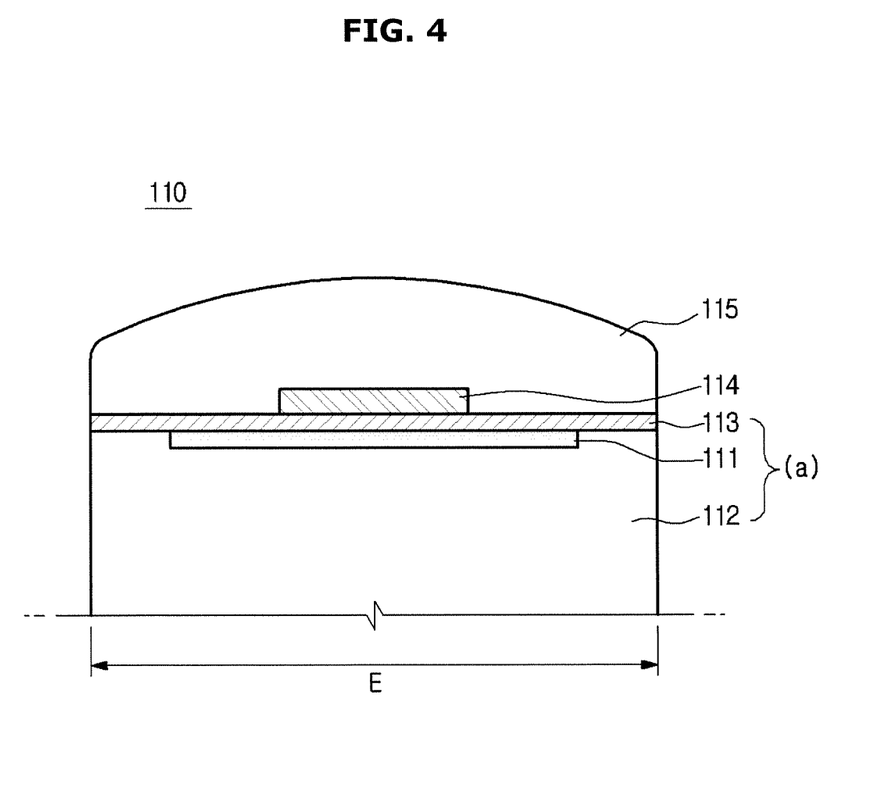
FIG. 4 is a cross-sectional view of a transducer module according to another exemplary embodiment, cut in the elevation direction.

FIG. 4 is a cross-sectional view of a transducer module according to another embodiment of the present disclosure, cut in the elevation direction E.

Referring to FIG. 4, a transducer module 110 according to another embodiment of the present disclosure may include: an acoustic module a including a piezoelectric layer 111, a backing layer 112 disposed below the piezoelectric layer 111, and a matching layer 113 disposed on the piezoelectric layer 111; an attenuation layer 114 disposed to cover the center upper surface of the acoustic module a; and a lens layer 115 disposed to cover the upper surface of the attenuation layer 114.

Details about the lens layer 115 and the acoustic module a including the piezoelectric layer 111, the backing layer 112, and the matching layer 113 have been described above with reference to FIG. 3, and accordingly, further detailed descriptions thereof will be omitted.

The attenuation layer 114 may be disposed to cover the center upper surface of the acoustic module a. The attenuation layer 114 may be formed with a low attenuation material or a low viscosity material in order to prevent ultrasonic waves generated by the piezoelectric layer 111 from attenuating. For example, the attenuation layer 114 may be formed with a silicon material having attenuation ranging from 3 dB/cm to 15 dB/cm with respect to ultrasonic waves having a frequency of 5 MHz or a driving signal of the transducer module 110. As such, by forming the attenuation layer 114 with a low attenuation material, it is possible to improve the sensitivity of ultrasonic waves.

The attenuation layer 114 may be disposed to cover the center upper surface of the acoustic module a, as seen in the elevation direction E.

In the current embodiment, a case in which the probe 100 includes a single lens layer 115 and a single attenuation layer 114 disposed on the center upper surface of the acoustic module a is shown, however, the probe 100 may include a plurality of lens layers 115 having different properties.

Figure 5:
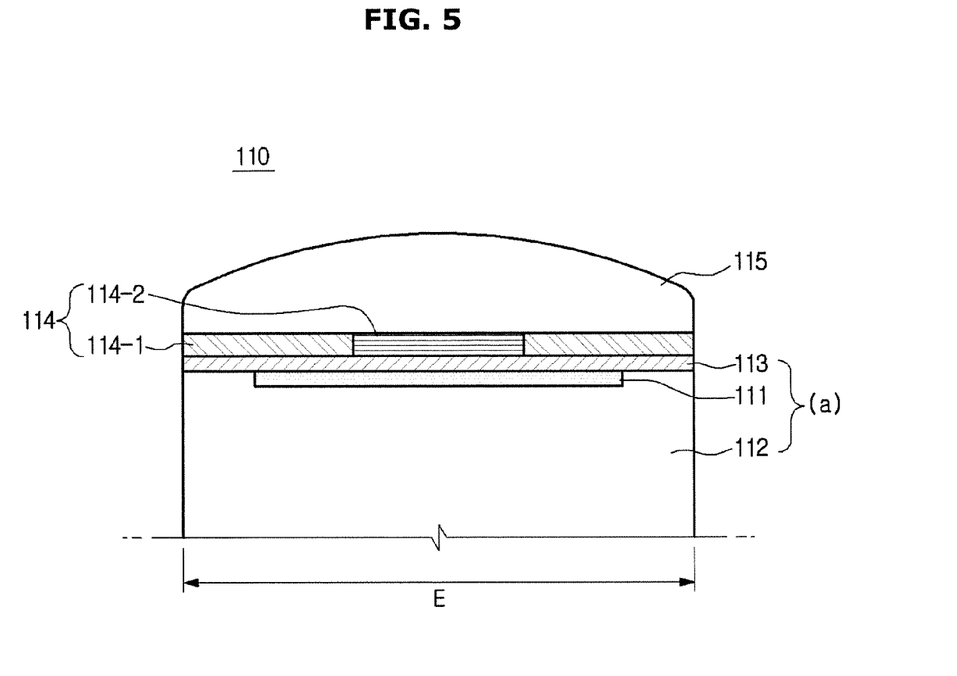
FIG. 5 is a cross-sectional view of a transducer module according to still another exemplary embodiment, cut in the elevation direction.

FIG. 5 is a cross-sectional view of a transducer module according to still another embodiment of the present disclosure, cut in the elevation direction E.

Referring to FIG. 5, a transducer module 110 according to still another embodiment of the present disclosure may include: an acoustic module a including a piezoelectric layer 111, a backing layer 112 disposed below the piezoelectric layer 111, and a matching layer 113 disposed on the piezoelectric layer 111; an attenuation layer 114 disposed to cover the upper surface of the acoustic module a; and a lens layer 115 disposed to cover the upper surface of the attenuation layer 114.

Details about the lens layer 115 and the acoustic module a including the piezoelectric layer 111, the backing layer 112, and the matching layer 113 have been described above with reference to FIG. 3, and accordingly, further detailed descriptions thereof will be omitted.

The attenuation layer 114 may be applied on the upper surface of the acoustic module a.

According to an embodiment, a center part 114-2 of the attenuation layer 114, as seen in the elevation direction E, may be formed with a low attenuation material or a low viscosity material, and left and right parts (that is, both edges 114-1) of the attenuation layer 114, as seen in the elevation direction E, may be formed with a high attenuation material or a high viscosity material.

For example, the center part 114-2 of the attenuation layer 114 may be formed with a silicon material having attenuation ranging from 3 dB/cm to 15 dB/cm with respect to ultrasonic waves having a frequency of 5 MHz or a driving signal of the transducer module 110, and the left and right parts 114-1 of the attenuation layer 114 may be formed with a silicon material having attenuation ranging from 20 dB/cm to 40 dB/cm with respect to ultrasonic waves having a frequency of 5 MHz or a driving signal of the transducer module 110.

In the current embodiment, a case in which the probe 100 includes a single lens layer 115 and an attenuation layer 114 disposed on the upper surface of the acoustic module a is shown, however, the probe 100 may include a plurality of lens layers 115 having different properties.

Also, according to another embodiment, all of the center part 114-2 and the left and right parts (that is, both edges 114-1) of the attenuation layer 114, as seen in the elevation direction E, may be formed with a low attenuation material or a low viscosity material, wherein the center part 114-2 may have a single-layer structure and the both edges 114-1 may each have a multi-layer structure, which are not shown in FIG. 5.

For example, any one layer of the center part 114-2 or the both edges 114-1 configuring the attenuation layer 114 may be formed with a silicon material having attenuation ranging from 3 dB/cm to 15 dB/cm with respect to ultrasonic waves having a frequency of 5 MHz or a driving signal of the transducer module 110.

Since the both edges 114-1 of the attenuation layer 114 each has a multi-layer structure, the both edges 114-1 of the attenuation layer 114 may have high attenuation ranging from 20 dB/cm to 40 dB/cm with respect to ultrasonic waves having a frequency of 5 MHz or a driving signal of the transducer module 110.

Figure 6:
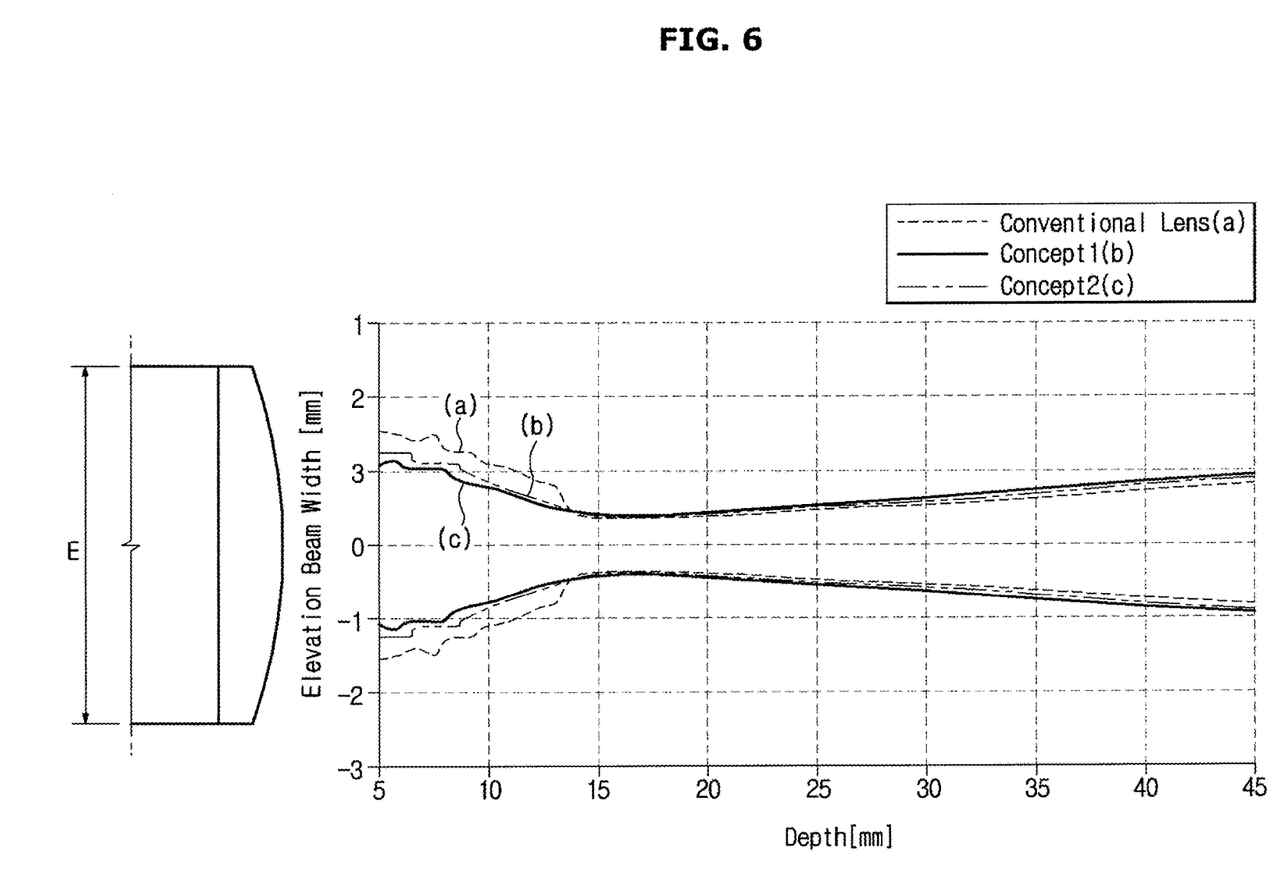
FIG. 6 shows examples of beam widths of ultrasonic waves transmitted from transducer modules according to exemplary embodiments.

FIG. 6 shows examples of beam widths of ultrasonic waves transmitted from the transducer modules 110 according to the embodiments shown in FIGS. 3 and 4.

When the attenuation layers 114 according to the embodiment of FIG. 3 are used ((b) of FIG. 6), a frequency band (that is, a bandwidth) of ultrasonic waves having greater sound pressure than predetermined sound pressure can become narrow in a short-range region compared to when no attenuation layer 114 according to the embodiments is used ((a) of FIG. 6).

Also, when the attenuation layer 114 according to the embodiment of FIG. 4 is used ((c) of FIG. 6), a bandwidth can become narrow in a short-range region compared to when no attenuation layer 114 according to the embodiments is used ((a) of FIG. 6).

Also, when the attenuation layer 114 according to the embodiment of FIG. 5 in which the embodiment of FIG. 3 is combined with the embodiment of FIG. 4 is used, a bandwidth can become narrow in a short-range region.

In addition, when any one of the attenuation layers 114 according to the embodiments of FIGS. 3, 4, and 5 is used, unnecessary side lobes of ultrasonic waves sound pressure in the elevation direction E can be reduced in a short-range region.

Hereinafter, a method of manufacturing a transducer module according to an embodiment of the present disclosure will be described with reference to FIGS. 7, 8, and 9.

Figure 7:
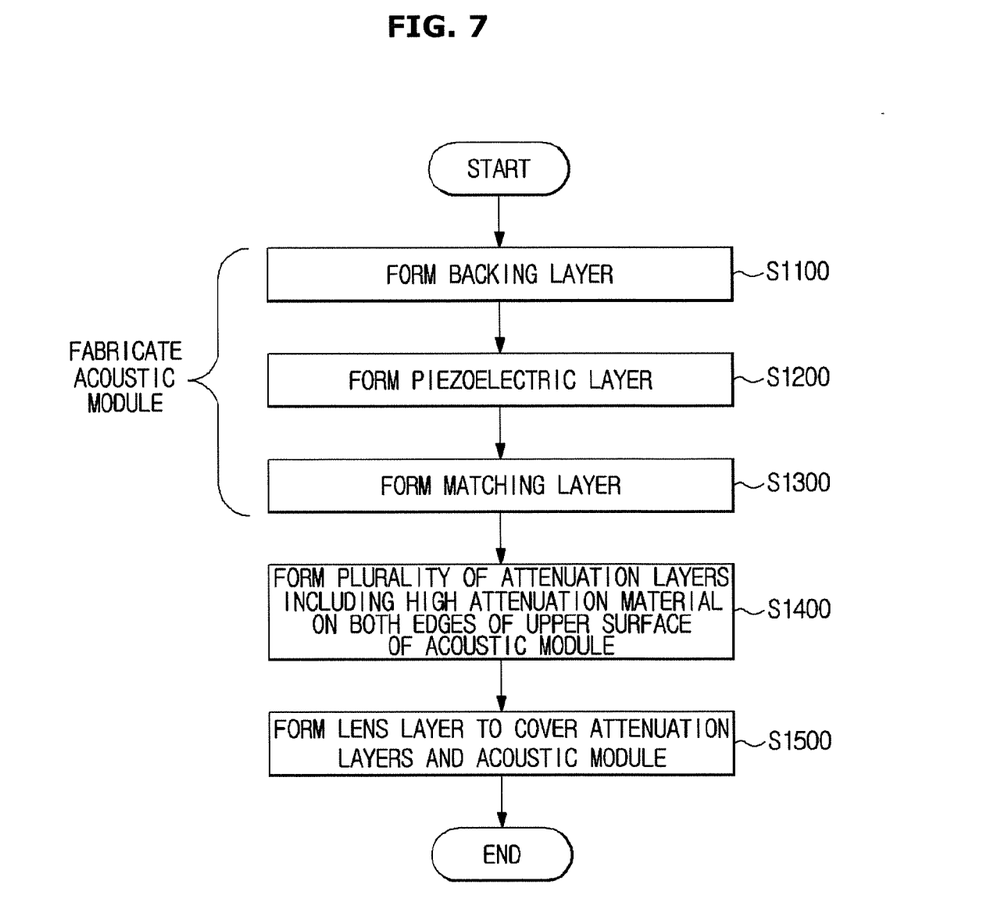
FIG. 7 is a flowchart illustrating a method of manufacturing a transducer module according to an exemplary embodiment.

FIG. 7 is a flowchart illustrating a method of manufacturing a transducer module according to an embodiment of the present disclosure.

First, the backing layer 112 may be formed, in operation S1100.

Then, the piezoelectric layer 111 may be formed to cover the upper surface of the backing layer 112, in operation S1200.

The piezoelectric layer 111 may be formed with a piezoelectric material to convert electrical signals into mechanical vibrations to generate ultrasonic waves.

The piezoelectric material may be a ceramic of PZT, a PZMT single crystal containing a solid solution of lead magnesium niobate and lead titanate, or a PZNT single crystal containing a solid solution of lead zincniobate and lead titanate.

The piezoelectric layer 111 may have a single-layer structure or a multi-layer structure.

According to an embodiment, the piezoelectric layer 111 may be formed to cover the upper surface of the backing layer 112. In this case, the piezoelectric layer 111 may be formed on the entire upper surface of the backing layer 112 such that an area and a height in elevation direction E of the piezoelectric layer 111 are respectively equal to an area and a height in elevation direction E of the backing layer 112. Alternatively, the piezoelectric layer 111 may be formed on a part of the upper surface of the backing layer 112 such that an area and a height in elevation direction E of the piezoelectric layer 111 are smaller than an area and a height in elevation direction E of the backing layer 112.

According to another embodiment, the piezoelectric layer 111 may be formed to cover a caved surface of the backing layer 112 formed by removing a part of the backing layer 112.

Meanwhile, it is also possible that the piezoelectric layer 111 is first formed, and the backing layer 112 is molded or attached on the lower surface of the piezoelectric layer 111.

Then, the matching layer 113 may be formed to cover the upper surface of the piezoelectric layer 111, in operation S1300.

As such, by forming the backing layer 112, the piezoelectric layer 111, and the matching layer 113 sequentially, the acoustic module a may be formed.

Then, the plurality of attenuation layers 114 including a high attenuation material may be formed on both edges of the upper surface of the acoustic module a, in operation S1400.

According to an embodiment, the attenuation layers 114 may be formed with a high attenuation material or a high viscosity material in order to attenuate ultrasonic waves generated by the piezoelectric layer 111. For example, the attenuation layers 114 may be formed with a silicon material having attenuation ranging from 20 dB/cm to 40 dB/cm with respect to ultrasonic waves having a frequency of 5 MHz or a driving signal of the transducer module 110.

Also, the attenuation layers 114 may be formed as multi-layer structures, each layer formed with a low attenuation material or a low viscosity material, at both edges of the upper surface of the acoustic module a. In this case, the attenuation layer 114 formed as the multi-layer structure may have a high attenuation property like a high attenuation material to attenuate ultrasonic waves.

The low attenuation material or the low viscosity material forming any one layer of the multi-layer structure of the attenuation layers 114 may be a silicon material having attenuation ranging from 3 dB/cm to 15 dB/cm with respect to ultrasonic waves having a frequency of 5 MHz or a driving signal of the transducer module 110.

The attenuation layers 114 may be, when the upper surface of the acoustic module a is divided into a left upper surface and a right upper surface as seen in the elevation direction E, arranged to cover a part of the left upper surface and a part of the right upper surface. For example, the attenuation layers 114 may be arranged to cover the most left upper part of the left upper surface and the most right upper part of the right upper surface.

Then, the lens layer 115 may be formed to cover the upper surfaces of the attenuation layers 114 and the upper surface of the acoustic module a, in operation S1500.

The lens layer 115 may be formed with a material that has high wear resistance and can propagate ultrasonic waves at high speed in order to focus ultrasonic waves and protect the acoustic module a, specifically, the piezoelectric layer 111. The lens layer 115 may have a convex shape in the transmission direction of ultrasonic waves in order to focus ultrasonic waves. However, the lens layer 115 may have a concave shape if the velocity of sound in the air is lower than that in the object ob.

Figure 8:
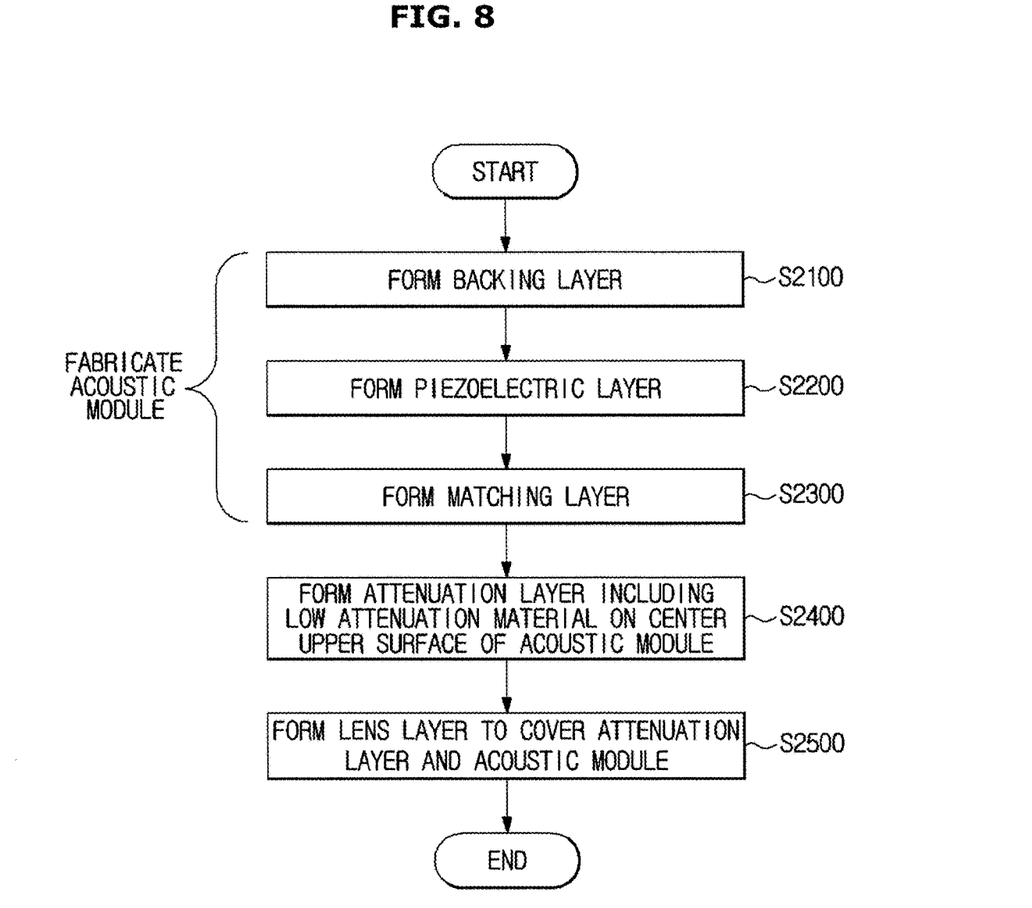
FIG. 8 is a flowchart illustrating a method of manufacturing a transducer module according to another exemplary embodiment.

FIG. 8 is a flowchart illustrating a method of manufacturing a transducer module according to another embodiment of the present disclosure.

Operation S2100 of forming the backing layer 112, operation S2200 of forming the piezoelectric layer 111, operation S2300 of forming the matching layer 113, and operation S2500 of forming the lens layer 115 to cover the attenuation layer 114 have been described above with reference to FIG. 7, and accordingly, further descriptions thereof will be omitted.

Likewise, in the embodiment of FIG. 8, it is also possible that the piezoelectric layer 111 is first formed, and the backing layer 112 is molded or attached on the lower surface of the piezoelectric layer 111.

After operation S2300 of forming the matching layer 113, the attenuation layer 114 including a low attenuation material may be formed on the center upper surface of the acoustic module a, in operation S2400.

According to another embodiment, the attenuation layer 114 may be formed with a low attenuation material or a low viscosity material in order to prevent ultrasonic waves generated by the piezoelectric layer 111 from attenuating. For example, the attenuation layer 114 may be formed with a silicon material having attenuation ranging from 3 dB/cm to 15 dB/cm with respect to ultrasonic waves having a frequency of 5 MHz or a driving signal of the transducer module 110.

The attenuation layer 114 according to another embodiment of the present disclosure may be formed to cover the center upper surface of the acoustic module a, as seen in the elevation direction E.

Figure 9:
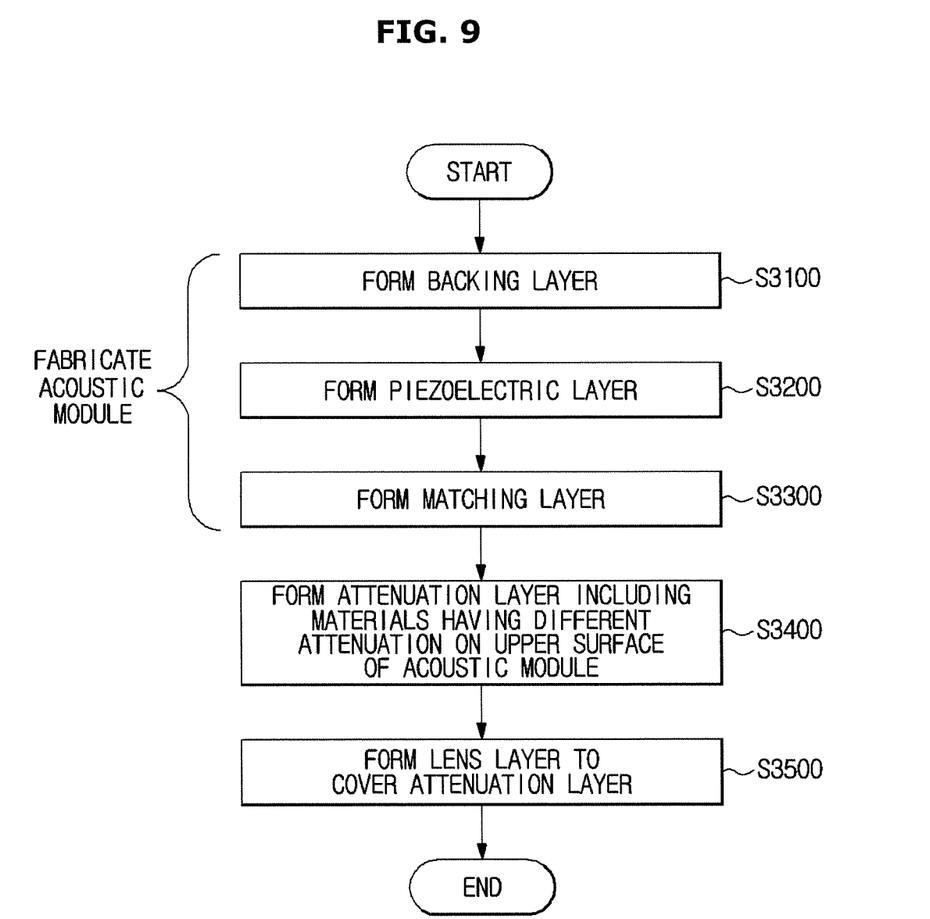
FIG. 9 is a flowchart illustrating a method of manufacturing a transducer module according to still another exemplary embodiment.

FIG. 9 is a flowchart illustrating a method of manufacturing a transducer module according to still another embodiment of the present disclosure.

Operation S3100 of forming the backing layer 112, operation S3200 of forming the piezoelectric layer 111, operation S3300 of forming the matching layer 113, and operation S3500 of forming the lens layer 115 to cover the attenuation layer 114 have been described above with reference to FIG. 7, and accordingly, further descriptions thereof will be omitted.

Likewise, in the embodiment of FIG. 9, it is also possible that the piezoelectric layer 111 is first formed, and the backing layer 112 is molded or attached on the lower surface of the piezoelectric layer 111.

According to an embodiment, after operation S3300 of forming the matching layer 113, the attenuation layer 114 may be formed with materials having different attenuation on the upper surface of the acoustic module a such that the materials of the different attenuation are applied at different areas of the upper surface of the acoustic module a, in operation S3400.

The attenuation layer 114 may be applied on the upper surface of the acoustic module a. At this time, the center part of the attenuation layer 114, as seen in the elevation direction E, may be formed with a low attenuation material or a low viscosity material, and a part of the left part of the attenuation layer 114 and a part of the right part of the attenuation layer 114 may be formed with a high attenuation material or a high viscosity material.

For example, the center part of the attenuation layer 114, as seen in the elevation direction E, may be formed with a silicon material having attenuation ranging from 3 dB/cm to 15 dB/cm with respect to ultrasonic waves having a frequency of 5 MHz or a driving signal of the transducer module 110, and a part of the left part of the attenuation layer 114 and a part of the right part of the attenuation layer 114 may be formed with a silicon material having attenuation ranging from 20 dB/cm to 40 dB/cm with respect to ultrasonic waves having a frequency of 5 MHz or a driving signal of the transducer module 110.

Also, according to another embodiment, the attenuation layer 114 including a low attenuation material may be formed on the enter upper surface of the acoustic module a, which is not shown in the drawings. In this case, the center part of the attenuation layer 114 may have a single-layer structure, and both edges of the attenuation layer 114 may have multi-layer structures.

For example, the center part of the attenuation layer 114, as seen in the elevation direction E, may be formed as a single-layer structure formed with a silicon material having attenuation ranging from 3 dB/cm to 15 dB/cm with respect to ultrasonic waves having a frequency of 5 MHz or a driving signal of the transducer module 110, and both edges of the attenuation layer 114 may each be formed as a multi-layer structure each layer formed with a silicon material having attenuation ranging from 3 dB/cm to 15 dB/cm with respect to ultrasonic waves having a frequency of 5 MHz or a driving signal of the transducer module 110. Accordingly, the thickness of the center part of the attenuation layer 114 may be thinner than those of both edges of the attenuation layer 114.

Since both edges of the attenuation layer 114 each has a multi-layer structure, a part of the left part of the attenuation layer 114 and a part of the right part of the attenuation layer 114, as seen in the elevation direction E, may have high attenuation ranging from 20 dB/cm to 40 dB/cm with respect to ultrasonic waves having a frequency of 5 MHz or a driving signal of the transducer module 110.

According to an aspect of the embodiments described above, by providing a high attenuation material at both edges of the upper surface of the acoustic module a, it is possible to reduce unnecessary side lobes upon transmission of ultrasonic waves, and to make a frequency band of ultrasonic waves having greater sound pressure than predetermined sound pressure become narrow in a short-range region.

According to another aspect of the embodiments described above, by providing a low attenuation material on the center upper surface of the acoustic module a, it is possible to reduce unnecessary side lobes upon transmission of ultrasonic waves, and to make a frequency band of ultrasonic waves having greater sound pressure than predetermined sound pressure become narrow in a short-range region.

According to still another aspect of the embodiments described above, by providing materials having different attenuation at different areas on the upper surface of the acoustic module, it is possible to reduce unnecessary side lobes upon transmission of ultrasonic waves, and to make a frequency band of ultrasonic waves having greater sound pressure than predetermined sound pressure become narrow in a short-range region.

The aforementioned descriptions are only for illustrative purposes, and it will be apparent that those skilled in the art can make various modifications thereto without changing the technical spirit and essential features of the present disclosure. Thus, it should be understood that the exemplary embodiments described above are merely for illustrative purposes and not for limitation purposes in all aspects. For example, each component described as a single type can be implemented in a distributed type, and components described as distributed can be implemented in a combined form.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A probe comprising:
   an acoustic module comprising a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer;
   an attenuation layer disposed on the center upper surface of the acoustic module, and including a low attenuation material; and a lens layer disposed to cover the upper surface of the attenuation layer, and configured to focus ultrasonic waves transmitted forward from the piezoelectric layer at a predetermined point.

2. The probe according to claim 1, wherein the attenuation layer is disposed on the center surface of the acoustic module, as seen in an elevation direction of the probe.

3. The probe according to claim 1, wherein the attenuation layer includes a silicon material.

4. The probe according to claim 1, wherein the piezoelectric layer is formed on a caved surface of the backing layer.

5. The probe according to claim 1, wherein the attenuation layer is configured with a plurality of layers, and the lens layer is configured with a plurality of layers.

6. The probe according to claim 1, wherein the piezoelectric layer is formed on the entire or a part of the upper surface of the backing layer.

7. A probe comprising:
an acoustic module comprising a piezoelectric layer configured to generate ultrasonic waves, a matching layer configured to reduce a difference in acoustic impedance between the piezoelectric layer and an object, and a backing layer configured to absorb ultrasonic waves generated by the piezoelectric layer and transmitted backward from the piezoelectric layer;
an attenuation layer disposed on the upper surface of the acoustic module, wherein a center part of the attenuation layer has ultrasonic waves attenuation that is different from ultrasonic waves attenuation of both edges of the attenuation layer; and
a lens layer disposed to cover the upper surface of the attenuation layer, and configured to focus ultrasonic waves transmitted forward from the piezoelectric layer at a predetermined point.

8. The probe according to claim 7, wherein the attenuation layer includes a low attenuation material at the center part as seen in an elevation direction of the probe, and a high attenuation material at both edges as seen in the elevation direction of the probe.

9. The probe according to claim 7, wherein the attenuation layer includes a low attenuation material, the center part of the attenuation layer as seen in an elevation direction of the probe has a single-layer structure, and both edges of the attenuation layer as seen in the elevation direction of the probe each has a multi-layer structure.

10. The probe according to claim 7, wherein the attenuation layer includes a silicon material.

11. The probe according to claim 7, wherein the piezoelectric layer is formed on a caved surface of the backing layer.

12. The probe according to claim 7, wherein the attenuation layer is configured with a plurality of layers, and the lens layer is configured with a plurality of layers.

13. A method of manufacturing a probe, comprising:
fabricating an acoustic module by forming a backing layer, a piezoelectric layer, and a matching layer sequentially;
forming an attenuation layer configured to attenuate ultrasonic waves generated by the acoustic module, and including a low attenuation material, on the center upper surface of the acoustic module; and
forming a lens layer configured to focus ultrasonic waves transmitted forward from the piezoelectric layer at a predetermined point, on the upper surface of the attenuation layer.

14. The method according to claim 13, wherein the forming of the attenuation layer comprises forming other attenuation layers with a high attenuation material respectively, at both edges of the upper surface of the acoustic module.

15. The method according to claim 14, wherein the high attenuation material includes a silicon material.

16. The method according to claim 14, wherein the forming of the other attenuation layers comprises forming the other attenuation layers respectively at a part of the left upper surface of the acoustic module and at a part of the right upper surface of the acoustic module, as seen in an elevation direction of the probe.

17. The method according to claim 16, wherein the forming of the other attenuation layers comprises forming the other attenuation layers respectively at the most left upper part of the left upper surface of the acoustic module and at the most right upper part of the right upper surface of the acoustic module.

18. The method according to claim 13, wherein the forming of the attenuation layer comprises forming a multi-layer structure each layer formed with a low attenuation material on the center upper surface of the acoustic module.

19. The method according to claim 13, wherein the fabricating of the acoustic module comprises removing a part of the backing layer, and forming the piezoelectric layer on a caved surface of the backing layer formed by removing the part of the backing layer.

20. The method according to claim 13, wherein the forming of the lens layer comprises configuring the lens layer with a plurality of layers.

* * * * *